United States Patent
Picozzi et al.

(10) Patent No.: US 7,161,030 B2
(45) Date of Patent: Jan. 9, 2007

(54) HYDROFLUOROETHERS HAVING AT LEAST ONE HYDROGENATED-OCFX'CH$_3$ END GROUP WHEREIN X'=F, CF$_3$ AND THEIR PREPARATION PROCESS

(75) Inventors: Rosaldo Picozzi, Milan (IT); Antonella Di Meo, Milan (IT); Claudio Tonelli, Milan (IT)

(73) Assignee: Solvay Solexis S.p.A., Milan (IT)

( * ) Notice: Subject to any disclaimer, the term of this patent is extended or adjusted under 35 U.S.C. 154(b) by 445 days.

(21) Appl. No.: 10/630,697

(22) Filed: Jul. 31, 2003

(65) Prior Publication Data
US 2004/0024249 A1   Feb. 5, 2004

(30) Foreign Application Priority Data
Aug. 1, 2002   (IT) .......................... MI2002A1731

(51) Int. Cl.
| | |
|---|---|
| C07C 51/58 | (2006.01) |
| C07C 41/18 | (2006.01) |
| C07C 45/41 | (2006.01) |
| C07C 53/15 | (2006.01) |

(52) U.S. Cl. .................. 562/586; 562/856; 568/486; 568/488; 568/489; 568/490; 568/615; 568/622

(58) Field of Classification Search .............. 568/486, 568/489, 488, 490, 615, 622; 562/586, 856
See application file for complete search history.

(56) References Cited

FOREIGN PATENT DOCUMENTS

| | | |
|---|---|---|
| EP | 0 657 211 A | 6/1995 |
| EP | 1 085 591 A | 3/2001 |
| EP | 1 170 275 A | 1/2002 |
| GB | 1 034 926 A | 7/1966 |
| WO | WO 99/47480 | 9/1999 ...................... 41/1 |

OTHER PUBLICATIONS

V.S. Yuminov, Polyfluorinated Ethers: IV. By-products in the Synthesis of Polyfluorinated Alkyl Vinyl Ethers in a Solvating Solvent, Russian Journal of Organic Chemistry, vol. 34, No. 12, Dec. 1998, pp. 1715-1720.*
Int'l Pub. No. WO 99 47480 A, Sep. 23, 1999, World Intellectual Property Organization.

* cited by examiner

Primary Examiner—Rosalynd Keys
(74) Attorney, Agent, or Firm—Arent Fox PLLC

(57) ABSTRACT

Hydrofluoroethers of formula:

$$\text{T-CFX'—O—R}_f\text{—CFX-T'} \qquad \text{(II)}$$

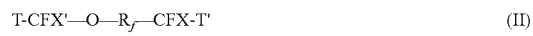

wherein:
T=CH$_3$;
X, X', equal to or different from each other, are selected between F, CF$_3$;
T00'=F, Cl, H, C$_1$–C$_3$ perfluoroalkyl, CH$_3$, CH$_2$OH, COCl, CHO, CO$_2$H;
R$_f$ is a perfluoroalkylene or a perfluoropolyoxyalkylene and respective preparation process by reduction with hydrogen in the presence of a platinum catalyst supported on metal fluorides of the corresponding compounds with at least one —COCl end group.

12 Claims, No Drawings

HYDROFLUOROETHERS HAVING AT LEAST ONE HYDROGENATED-OCFX'CH$_3$ END GROUP WHEREIN X'=F, CF$_3$ AND THEIR PREPARATION PROCESS

The present invention relates to hydrofluoroethers characterized in having at least one hydrogenated —OCFX'CH$_3$ end group wherein X'=F, CF$_3$ and their preparation process.

More specifically, the preparation process relates to the reduction with H$_2$, in the presence of platinum catalysts (Pt), of the corresponding fluorinated acylchloride precursors.

Hydrofluoroethers prepared by direct fluorination with F$_2$ or electrochemical fluorination of an ether compound or by alkylation of fluorinated alcohols are known.

In patent application WO 99/47,480 it is shwon that hydrofluoroethers can be obtained by alkylation of fluorinated carbonyl compounds. The above methods employ starting compounds having a low molecular weight with a number of carbon atoms equal to or lower than 12, besides they give low yields and selectivity, and do not give hydrofluoroethers having at least one OCFX'CH$_3$ end group with X'=F, CF$_3$.

More specifically patent application WO 99/47,480 describes an alkylation process of perfluorinated carbonyl compounds in the presence of a Lewis acid, for example SbF$_5$. Although in the general formula:

$$R_f\text{—}(O\text{—}R)_x \qquad (I)$$

wherein

R$_f$ is a fluorinated C$_1$–C$_{15}$ alkyl, optionally substituted and optionally containing heteroatoms in the chain as N, O, S;

R is a C$_1$–C$_{10}$ alkyl, optionally substituted, x ranges from 1 to 3, a great number of potential hydrofluoroethers is contained, really by the process only hydrofluoroethers having end groups different from —OCFX'CH$_3$ are obtainable. See the Examples of patent application WO 99/47,480. Therefore the compounds having —OCFX'CH$_3$ termination have not been prepared and no indication about how to prepare them is given. Accordingly the skilled man in the art on the basis of the aforesaid patent and of the common general knowledge is unable to prepare the compounds of the present invention.

Generally the reaction described in patent application WO 99/47,480 proceeds with very low conversions when R$_f$ is branched. The reaction shows the limitation that to obtain acceptable conversions it is necessary to use CH$_3$F as alkylating agent, has the drawback to require the use of Lewis acids which are aggressive and need the use of pressure resistant equipments built in special substances. Furthermore HF forms, producing further problems in the equipment choice. Since the alkylation reaction is an equilibrium reaction, it does not allow the obtainment of hydrofluoro-ethers with a high yield.

The Applicant has furthermore found that by using a Lewis acid as SbF$_5$, in the ratios suggested by patent application WO 99/47,480 and by following the same modalities suggested by the same, no hydrofluoroethers are obtained starting from precursors having a perfluoropolyether structure, in particular containing —OCF$_2$O— sequences; besides the use of SbF$_5$ amounts higher than those suggested causes the almost total degradation of the initial perfluoropolyether structure without obtaining however hydrofluoroethers (see the comparative Examples).

The need was therefore felt to obtain hydrofluoroethers by a process avoiding the prior art inconveniences and limitations.

It has been found a hydrogenation process of fluorinated precursors containing acylchloride groups carried out in the presence of platinum catalysts which allows to obtain hydrofluoroethers characterized in having at least one —OCFX'CH$_3$ end group and quantitative conversions with selectivity even of the order of 70%.

An object of the present invention are therefore hydrofluoroethers of formula:

$$T\text{-CFX'}\text{—}O\text{—}R_f\text{—CFX-T'} \qquad (II)$$

wherein:

T=CH$_3$;

X, X', equal to or different from each other, are selected from F, CF$_3$;

T'=F, Cl, H, C$_1$–C$_3$ perfluoroalkyl, CH$_3$, CH$_2$OH, COCl, CHO, CO$_2$H;

R$_f$ is selected from:

C$_2$–C$_{15}$ perfluoroalkylene;

—(C$_2$F$_4$O)$_m$(CF$_2$CF(CF$_3$)O)$_n$(CF$_2$O)$_p$(CF(CF$_3$)O)$_q$— wherein the sum n+m+p+q ranges from 2 to 200, the (p+q)/(m+n+p+q) ratio is lower than or equal to 10:100, preferably comprised between 0.5:100 and 4:100, the n/m ratio ranges from 0.2 to 6, preferably from 0.5 to 3; m, n, p, q are equal to or different from each other and when m, n range from 1 to 100, preferably from 1 to 80, then p, q range from 0 to 80, preferably from 0 to 50; the units with n, m, p, q indexes being statistically distributed along the chain;

—(CF$_2$CF$_2$CF$_2$O)$_r$— wherein r ranges from 2 to 200,

—(CF(CF$_3$)CF$_2$O)$_s$— wherein s ranges from 2 to 200,

The preferred structures of the perfluorooxyalkylene chain R$_f$ are selected from the following:

—(CF$_2$CF$_2$O)$_m$—(CF$_2$O)$_p$—,

—(CF$_2$CF(CF$_3$)O)$_n$—(CF$_2$O)$_p$—(CF(CF$_3$)O)$_q$ wherein the indexes have the above meanings.

A further object of the present invention is the preparation process of the formula (II) compounds comprising the reduction of the formula (III) corresponding precursors:

$$T''\text{-CFX'}\text{—}O\text{—}R_f\text{—CFX-T'''} \qquad (III)$$

wherein:

T''=COCl,

T'''=F, C$_1$–C$_3$ perfluoroalkyl, COCl, H, Cl,

X, X', R$_f$ are as defined in formula (II), carried out with gaseous hydrogen in the presence of a catalyst formed by supported platinum, preferably on metal fluorides, preferably in the presence of inert solvents, at a temperature in the range 20° C.–150° C., preferably 80° C.–120° C., at a pressure between 1 and 50 atm, preferably between 1 and 10 atm.

The formula (III) compounds having at least one —COCl end group are known, preparable for example by reaction of the corresponding PFPEs having —COF or —COOH end groups with inorganic chlorides or chlorinating agents such as thionyl chloride; preferably they are prepared according to what described in Italian patent applications MI2002A 001733 and MI2002A 001734 filed at the same time as the present application, and herein incorporated by reference, by a solid-liquid reaction between a large excess of inorganic chloride, CaCl$_2$ and a PFPE acylfluoride, at a temperature higher than 100° C., under strong stirring or alternatively a PFPE acylfluoride can be hydrolyzed obtaining the corresponding carboxylic acid which is subsequently treated with SOCl$_2$, in the presence of a tertiary amine, at a temperture in the range 50–100° C., obtaining the corresponding acylchloride.

The formula (II) hydrofluoroethers can alternatively be obtained from the corresponding PFPEs having at least one —CHO or —CH(OH)O(CH$_2$)$_t$R end group wherein t=0 or 1 and R is a C$_1$–C$_{10}$ alkyl group, H, or R$_f$.

The process can be carried out in a continuous or discontinuous way.

The metal fluorides are preferably selected from the group formed by CaF$_2$, BaF$_2$, MgF$_2$, AlF$_3$; more preferably CaF$_2$.

The Pt concentration on the support is comprised beteeen 0.1% and 10% with respect to the total weight of the catalyst, preferably between 1% and 2% by weight.

The used catalyst amount is in the range 1%–100% by weight with respect to the weight of the formula (III) compound, preferably 10%–100% by weight.

The inert solvents can for example be linear or cyclic perfluorinated ethers such for example perfluorotetrahydrofuran, perfluorotetrahydropyran, or their mixtures.

The invention hydrofluoroethers having at least one —OCFX'CH$_3$ end group with X'=F, CF$_3$ can be used as refrigerants, solvents in cleaning processes of printed circuits, and degreasing in vapour phase of metal components as substituents of CFCs, HCFCs and PFCs, resulted harmful for the ozone layer or show a high GWP (greenhouse potential).

Besides they found application for the wide range of utilization temperatures as substituents of HFCs which in some cases have a limited application as refrigerants due to their very low boiling temperature or their very high freezing point.

The following Examples are given for illustrative and not limitative purposes of the present invention.

EXAMPLES

Example 1

In a 1,000 ml flask, equipped with mechanical stirrer, bubbling pipe to introduce hydrogen/nitrogen, condenser with a bubble-counter 36.7 g of Pt supported on CaF$_2$ (Pt=1.5% by weight), 400 ml of mixture 1:1 of perfluorobutyltetrahydrofuran and perfluoropropyltetrahydropyran (D100), are introduced.

By external heating with thermostated oil bath, the solvent is brought to the boiling temperature (100° C.), then hydrogen is fed at atmospheric pressure at a flow-rate of 20 l/h, and 36.7 g of perfluoropolyether (PFPE) acylchloride of formula (IV)

  (IV)

wherein n/p=25 and n, p are integers such that the number average molecular weight is 400, are fed by dropping funnel in 30 minutes.

When the PFPE-COCl feeding is over, the reduction is let complete for 15 minutes in hydrogen flow.

It is then cooled to room temperature in nitrogen flow. The raw reaction compound is filtered to recover the catalyst.

The NMR ($^{19}$F and $^1$H) analysis of the compound shows a 100% conversion of the starting PFPE-acylchloride and a yield in formula (V) hydrofluoroether of 60% by moles:

  (V)

The NMR analysis shows furthermore the resence of the alcoholic compound of structure (VI) in an amount equal to 40% by moles:

  (VI)

To separate the hydrofluoroether (V) from the alcohol (VI), the raw reaction compound is chromatographed on silica gel using D 100 as eluent. From the extract, after solvent distillation, 18 g of a compound are obtained which by the NMR ($^{19}$F and $^1$H) analysis shows to be the hydrofluoroether of formula (V).

Example 2

In the same equipment of the Example 1
32.5 g of Pt supported on CaF$_2$ (Pt=1.5%),
150 ml of D100, are introduced.

One operates as described in the Example 1, by feeding 38.9 g of PFPE-acylchloride of formula (VII):

  (VII)

wherein n=3 and the number average molecular weight equal to 647.

The NMR ($^{19}$F and $^1$H) analysis of the compound shows a 100% conversion of the starting PFPE-acylchloride and a yield of 70% by moles in hydrofluoroether of formula (VIII):

  (VIII)

The NMR analysis shows furthermore the presence of the alcohol compound in an amount equal to 30% by moles, having structure (IX):

Cl(CF$_2$CF(CF$_3$)O)$_n$CF$_2$CH$_2$OH  (IX)

To separate the hydrofluoroether from the alcohol, the raw reaction compound is chromatographed on silica gel using D 100 as eluent. From the extract, after solvent distillation, 23 g of a compound are obtained which by the NMR ($^{19}$F and $^1$H) analysis shows to be the hydrofluoroether of formula (VIII).

The experimentation is repeated with the same modalities feeding each time 38 g of the acylchloride of the Example 2 by using the same catalyst of the preceding test.

After a cycle of 10 consecutive tests no variation of the reaction conversion and selectivity has been obtained and therefore no catalyst deactivation was evident.

Example 3

In a 100 ml flask equipped with mechanical stirrer, bubbling pipe to introduce hydrogen/nitrogen, condenser with bubble-counter, 1 g of Pt supported on C (Pt=5%), 40 ml of D100, are introduced.

One operates as described in the Example 1, by feeding 3.54 g of PFPE-acylchloride of the Example 2.

The NMR ($^{19}$F and $^1$H) analysis of the compound shows a partial conversion of the starting PFPE-acylchloride (53% by moles) and the converted compound shows to be a mixture of compounds of which the formula (VIII) hydrofluoroether forms the 64% by moles.

The difference to 100 is constituted by the acid of formula (X):

  (X)

Example 4

In the same equipment of the Example 1
30.4 g of Pt on $CaF_2$ (Pt=1.5%)
150 ml of D100, are introduced.

One operates as described in the Example 1, by feeding 35.2 g of PFPE-acylchloride of formula (XI):

$$ClOCCF_2O(CF_2CF_2O)_m(CF_2O)_pCF_2COCl \qquad (XI)$$

wherein m/p=1 and m, p are such that the number average molecular weight is 2,030.

The NMR ($^{19}F$ and $^1H$) analysis of the compound shows a 100% conversion of the starting PFPE-acylchloride obtaining a reaction mixture which on an average has 60% by moles of —$CF_2CH_3$ end groups, 32% of —$CF_2CH_2OH$ end groups, 8% of —$CF_2CO_2H$ end groups.

From the mixture, after chromatography on silica and solvent distillation, 5.8 g of hydrofluoroether of formula:

$$CH_3CF_2O(CF_2CF_2O)_n(CF_2O)_mCF_2CH_3 \qquad (XII),$$

12 g of PFPE of formula:

$$CH_3CF_2O(CF_2CF_2O)_m(CF_2O)_mCF_2CH_2OH \qquad (XIII),$$

9.7 g of PFPE-alcohol of formula:

$$HOCH_2CF_2O(CF_2CF_2O)_m(CF_2O)_pCF_2CH_2OH \qquad (XIV),$$

and 2.4 g of PFPE-acid of formula (XV):

$$HO(O)CCF_2O(CF_2CF_2O)_m(CF_2O)_pCF_2C(O)OH \qquad (XV),$$

are obtained.

Example 5

In the same equipment of the Example 3
3.26 g of Pt on $CaF_2$ (Pt=1.5%),
40 ml of D100, are introduced.

One operates as described in the Example 1, by feeding 3.21 g of PFPE-aldehyde of formula (XVI):

$$H(O)CCF_2O(CF_2CF_2O)_m(CF_2O)_pCF_2C(O)H \qquad (XVI)$$

wherein m/p=1 and m, p are such that the number average molecular weight is 2,000.

The NMR ($^{19}F$ and $^1H$) analysis of the compound shows a 100% conversion of the starting PFPE-aldehyde with the obtainment of a reaction mixture which on an average has 30% by moles of —$CF_2CH_3$ end groups and 70% of —$CF_2CH_2OH$ groups.

Example 6

In the same equipment of the Example 3
2.9 g of Pt on $CaF_2$ (Pt=1.5%),
40 ml of D100, are introduced.

One operates as described in the Example 1, by feeding 2.48 g of hydrated PFPE-aldehyde of formula:

$$(HO)_2HCCF_2O(CF_2CF_2O)_m(CF_2O)_pCF_2CH(OH)_2 \qquad (XVII)$$

wherein m/p=1 and m, p are such that the number average molecular weight is 2,000.

The NMR ($^{19}F$ and $^1H$) analysis of the compound shows a 100% conversion of the starting hydrated PFPE-aldehyde with the obtainment of a reaction mixture which on an average has 14% by moles of —$CF_2CH_3$ end groups and 86% of —$CF_2CH_2OH$ groups.

Example 7 (Comparative)

In the same equipment of the Example 3
4 g of Pt on $CaF_2$ (Pt=1.5%),
40 ml of D100, are introduced.

By operating as described in the Example 1, 4 g of PFPE-alcohol of formula:

$$Cl(CF_2CF(CF_3)O)_nCF_2CH_2OH \qquad (IX)$$

are fed, wherein n=3 and number average molecular weight equal to 604.

The compound NMR ($^{19}F$ and $^1H$) shows that no reaction has taken place, only the PFPE-alcohol of formula (IX) being present.

Example 8 (Comparative)

In the same equipment of the Example 3
4 g of Pt on $CaF_2$ (Pt=1.5%),
40 ml of D100, are introduced.

By operating as described in the Example 1, 4 g of PFPE-alcohol of formula:

$$HOCH_2CF_2O(CF_2CF_2O)_m(CF_2O)_pCF_2CH_2OH \qquad (XIV)$$

are introduced, wherein m/p=1 and m, p are such that the number average molecular weight is 2,000.

The NMR ($^{19}F$ and $^1H$) of the compound shows that no reaction has taken place, only the PFPE-alcohol of formula (XIV) being present.

Example 9 (Comparative)

In the same equipment of Example 3
60 mg of Pt black,
40 ml of D100, are introduced.

By operating as described in the Example 1, 4 g of PFPE-acylchloride of formula (VII) of the Example 2, are introduced.

The NMR ($^{19}F$ and $^1H$) of the compound shows that no reaction has taken place, only the PFPE-acylchloride of formula (VII) being present.

Example 10 (Comparative)

A 250 ml AISI 316 reactor equipped with magnetic stirring, bubbling pipe, thermocouple for the temperature reading and manometer, is dried at 70° C. under vacuum for 7 hours. It is then transferred in dry-box and fed with:

47 mg of $SbF_5$,
10 g of PFPE-acyl fluoride of formula:

$$FC(O)CF_2O(CF_2CF_2O)_m(CF_2O)_pCF_2C(O)F \qquad (XVIII)$$

wherein m/p=2.13 and m, p such that the number average molecular weight is 1,529.

The reactor is reassembled in the dry-box and cooled to −80° C. After the reactor has been put under vacuum, 1.82 g of gaseous $CH_3CF_3$ are fed. Then one operates by letting the reaction mixture reach the room temperature, then heating it to 30° C. and leaving it for 45 minutes at said temperature. The reactor is then cooled again to −30° C. and after 20 minutes the reaction mixture is quenched by the addition of 8 g of anhydrous methanol. It is brought to room temperature, then the reaction raw compound is discharged from the reactor. The methanol excess is removed by distillation at reduced pressure. 8.9 g of a compound are obtained, which at the $^{19}$F and $^1$H NMR analysis shows to be only a PFPE-ester of formula:

$$CH_3OC(O)CF_2O(CF_2CF_2O)_m(CF_2O)_pCF_2C(O)OCH_3 \quad (XIX)$$

i.e. the reaction compound between the starting PFPE-acylfluoride and the methyl alcohol.

Therefore no formation of hydrofluoroether has been noticed.

Example 11 (Comparative)

In the same equipment of the Example 10 and proceeding as described in the Example 10, the acid catalyst amount is increased by feeding:
2.2 g of SbF$_5$,
10.5 g of PFPE-acylfluoride of the Example 10.

It is cooled to $-80°$ C. noticing a residual pressure of 1.5 bar. One proceeds however as described in the Example 10 by feeding 1.82 g of CH$_3$CF$_3$. A further pressure increase is observed. After quenching with methanol at low temperature, it is let reach again the room temperature. The gas is sampled and is analyzed by gas-mass. It shows to be constituted by a mixture of decomposition compounds of the PFPE-acylfluoride chain, having low number average molecular weight (MW$\leq$500).

None of these shows hydrofluoroether structure with —OCF$_2$CH$_3$ end groups.

The liquid reaction mass gives only 2.5 g of PFPE-ester of formula:

$$CH_3OC(O)CF_2O(CF_2CF_2O)_m(CF_2O)_pCF_2C(O)OCH_3 \quad (XIX)$$

wherein m/p=5 and m, p are such that the number average molecular weight is 1,371.

The invention claimed is:

1. A process for the preparation or hydrofluoroethers of formula:

$$\text{T-CFX'—O—R}_f\text{—CFX-T'} \quad (II)$$

wherein:
T=CH$_3$;
X,X', equal to or different from each other, are selected between F, CF$_3$;
T'=F, Cl, H, C$_1$–C$_3$ perfluoroalkyl, CH$_3$, CH$_2$OH, COCl, CHO, CO$_2$H;
R$_f$ is selected from:
C$_2$–C$_{15}$ perfluoroalkylene;
—(C$_2$F$_4$O)$_m$(CF$_2$CF(CF$_3$)O)$_n$(CF$_2$O)$_p$(CF(CF$_3$)O)$_q$—
wherein
the sum n+m+p+q ranges from 2 to 200,
the (p+q)/(m+n+p+q) ratio is lower than or eaual to 10:100, the n/m ratio ranges from 0.2 to 6; m, n, p, q are equal to or different from each other and when m, n range from 1 to 100, then p, q range from 0 to 80; the units with n, m, p, q indexes being statistically distributed along the chain;
—(CF$_2$CF$_2$CF$_2$O)$_r$—wherein r ranges from 2 to 200,
—(CF(CF$_3$)CF$_2$O)$_s$—wherein s ranges from 2 to 200,
comprising the reduction of the formula (III) corresponding precursors:

$$\text{T''-CFX'—O—R}_f\text{—CFX-T'''} \quad (III)$$

wherein:
T''=COCl,
T'''=F, C$_1$–C$_3$ perfluoroalkyl, COCl, H, Cl,
X, X', R$_f$ are as defined in formula, carried out with gaseous hydrogen in the presence of a catalyst formed by supported platinum, at a temperature in the range 20° C.–15° C., at a pressure between 1 and 50 atm.

2. A process according to claim 1, wherein the metal fluorides are selected from the group formed by CaF$_2$, BaF$_2$, MgF$_2$, AlF$_3$.

3. A process according to claim 1, wherein the Pt concentration on the support is comprised between 0.1% and 10% with respect to the total weight of the catalyst.

4. A process according to claim 1, wherein the catalyst is used in an amount in the range 1%–100% by weight with respect to the weight of the formula (III) compound.

5. A process according to claim 1, wherein the inert solvent is selected among perfluorotetrahydrofuran, perfluorotetrahydropyran, or their mixtures.

6. A process according to claim 1, wherein the reduction of the formula (III) corresponding precursors is carred out with gaseous hydrogen in the presence of a catalyst formed by supported platinum on metal fluorides.

7. A process according to claim 1, wherein the reduction of the formula (III) corresponding precursos is carried out with gaseous hydrogen in the presence of a catalyst formed by supported platinum in the presence of inert solvents.

8. A process according to claim 1, wherein the temperature is in the range 80° C.–120 C.

9. A process according to claim 1, wherein the pressure is between 1 and 10 atm.

10. A process according to claim 2, wherein the metal fluorides are CaF$_2$.

11. A process according to claim 3, wherein the Pt concentration on the support is comprised between 1% and 2% by weight with respect to the total weight of the catalyst.

12. A process according to claim 4, wherein the catalyst is used in an amount in the range 10%–100% by weight with respect to the weight of the formula (III) compound.

* * * * *